(12) United States Patent
Lassetter et al.

(10) Patent No.: US 10,267,350 B2
(45) Date of Patent: Apr. 23, 2019

(54) INTEGRATED ARMBOARD AND WRIST SUPPORT APPARATUSES AND METHODS OF USE

(71) Applicants: John E Lassetter, Idaho Falls, ID (US); Philip Benz, Portland, OR (US); Matthew Semler, Portland, OR (US)

(72) Inventors: John E Lassetter, Idaho Falls, ID (US); Philip Benz, Portland, OR (US); Matthew Semler, Portland, OR (US)

(73) Assignee: Semler Technologies, Inc., Milwaukie, OR (US)

( * ) Notice: Subject to any disclaimer, the term of this patent is extended or adjusted under 35 U.S.C. 154(b) by 699 days.

(21) Appl. No.: 14/824,347

(22) Filed: Aug. 12, 2015

(65) Prior Publication Data

US 2017/0042751 A1 Feb. 16, 2017

(51) Int. Cl.
*A61F 5/37* (2006.01)
*A61G 13/12* (2006.01)
*F16B 45/00* (2006.01)

(52) U.S. Cl.
CPC .............. *F16B 45/00* (2013.01); *A61F 5/37* (2013.01); *A61G 13/124* (2013.01); *A61G 13/129* (2013.01); *A61G 13/1285* (2013.01); *A61G 2200/327* (2013.01)

(58) Field of Classification Search
CPC ........ A61F 5/0118; A61F 5/013; A61F 5/058; A61F 5/05825; A61F 5/05841; A61F 5/05858; A61F 5/05866; A61F 5/37; A61F 5/3761; A61F 5/3769; A61F 5/3792; A61F 2005/0132–2005/0179; A61F 5/0104; A61F 5/01–5/05875; A61G 7/065; A61G 7/075; A61G 13/00; A61G 13/0036; A61G 13/0045; A61G 13/12; A61G 13/1205; A61G 13/1235; A61G 13/1247; A61G 7/1082; A61G 7/1092–7/1094; A61G 13/10–13/101; A61G 13/124; A61G 13/126; A61G 13/128–13/1295; A61G 5/12; A61G 5/125; A61G 5/127; A61G 5/128; A47C 1/03; A47C 1/0307; A47C 1/0308; A47C 7/54; A47C 7/541; A47C 7/543; A47C 7/546

See application file for complete search history.

(56) References Cited

U.S. PATENT DOCUMENTS

| | | | |
|---|---|---|---|
| 4,576,351 A * | 3/1986 | Brink | A47C 1/03 248/118 |
| 4,996,977 A * | 3/1991 | Tiedeken | A61F 5/3761 128/878 |
| 5,718,671 A * | 2/1998 | Bzoch | A61G 5/12 128/878 |
| 2004/0158926 A1* | 8/2004 | Stevens | A61B 6/0442 5/623 |

* cited by examiner

*Primary Examiner* — Victoria J Hicks
*Assistant Examiner* — Michelle J Lee

(57) ABSTRACT

The present invention includes an apparatus, to be used during a medical procedure to support a patient's arm, which generally includes an armboard and an optional wrist support device attached to a patient that may be removably connected to the armboard, and a general method of use.

15 Claims, 7 Drawing Sheets

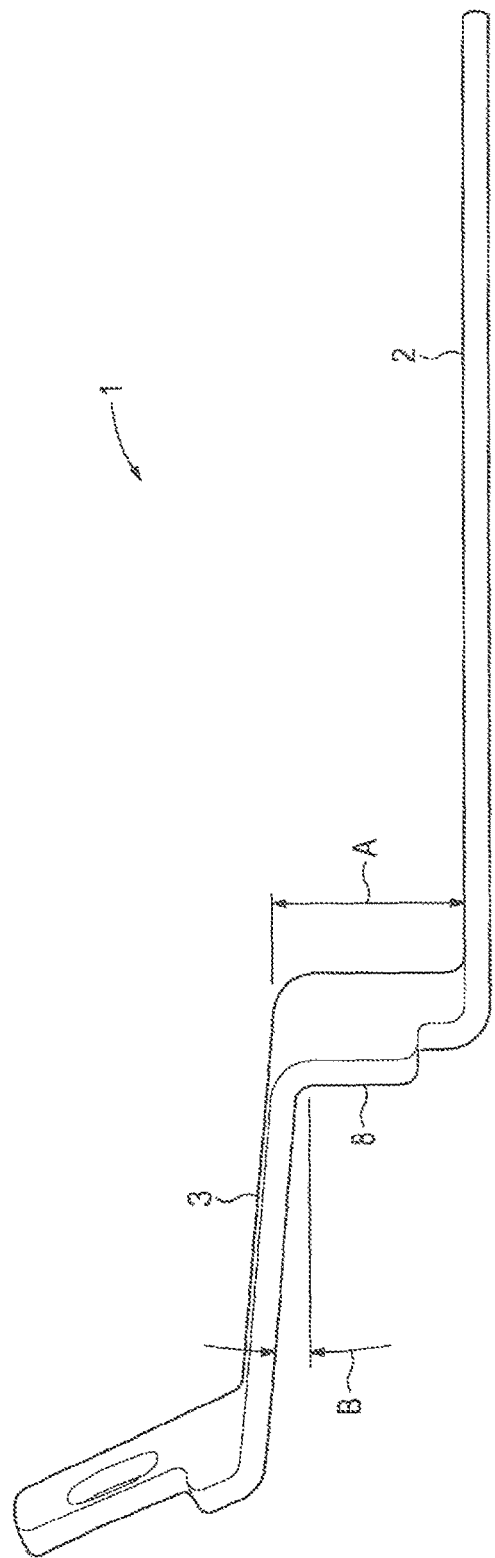

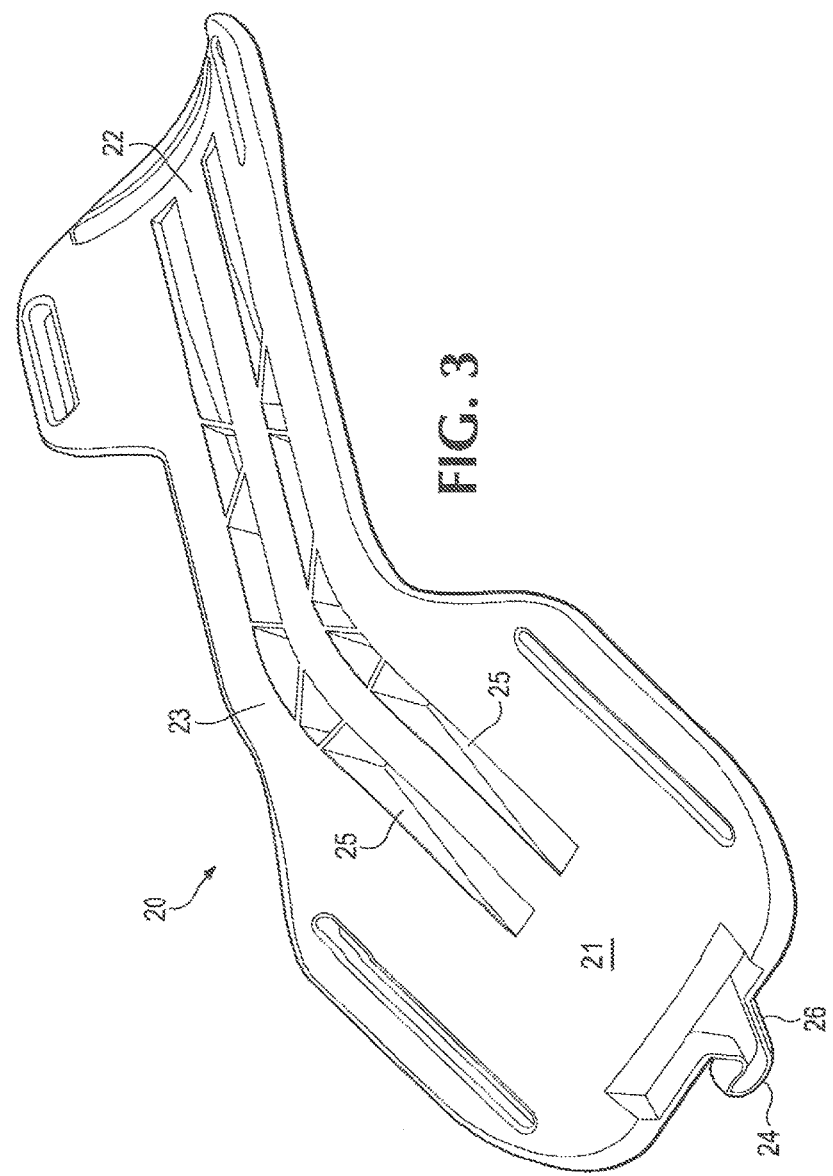

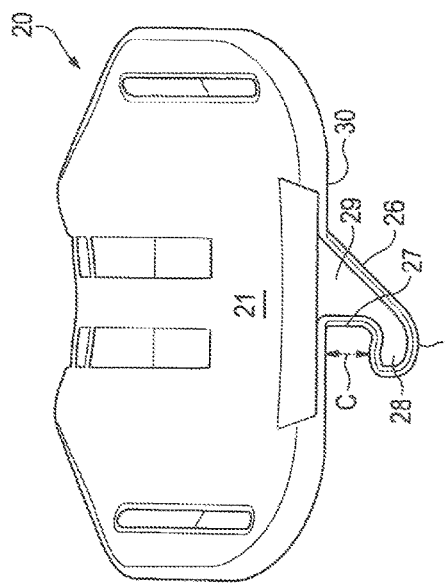
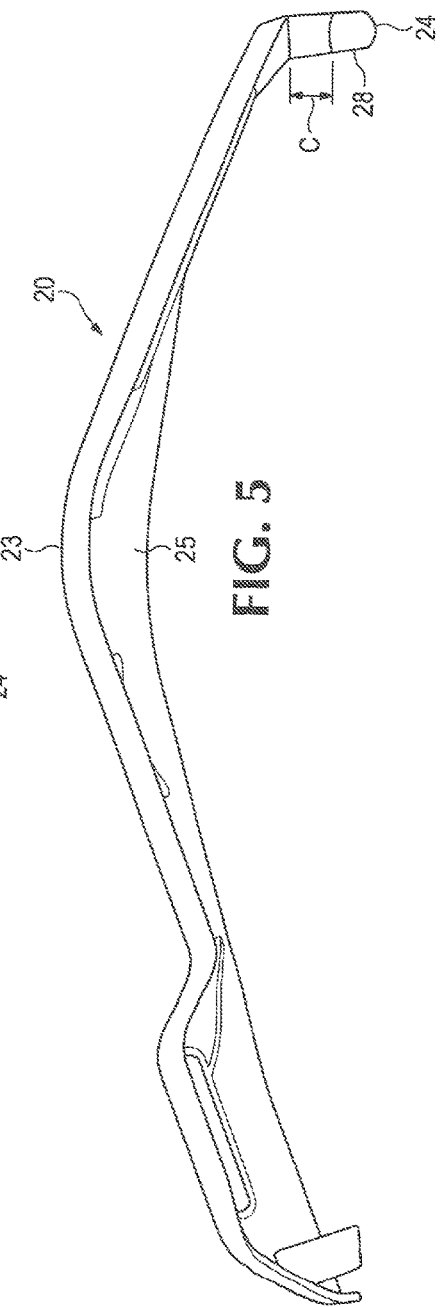

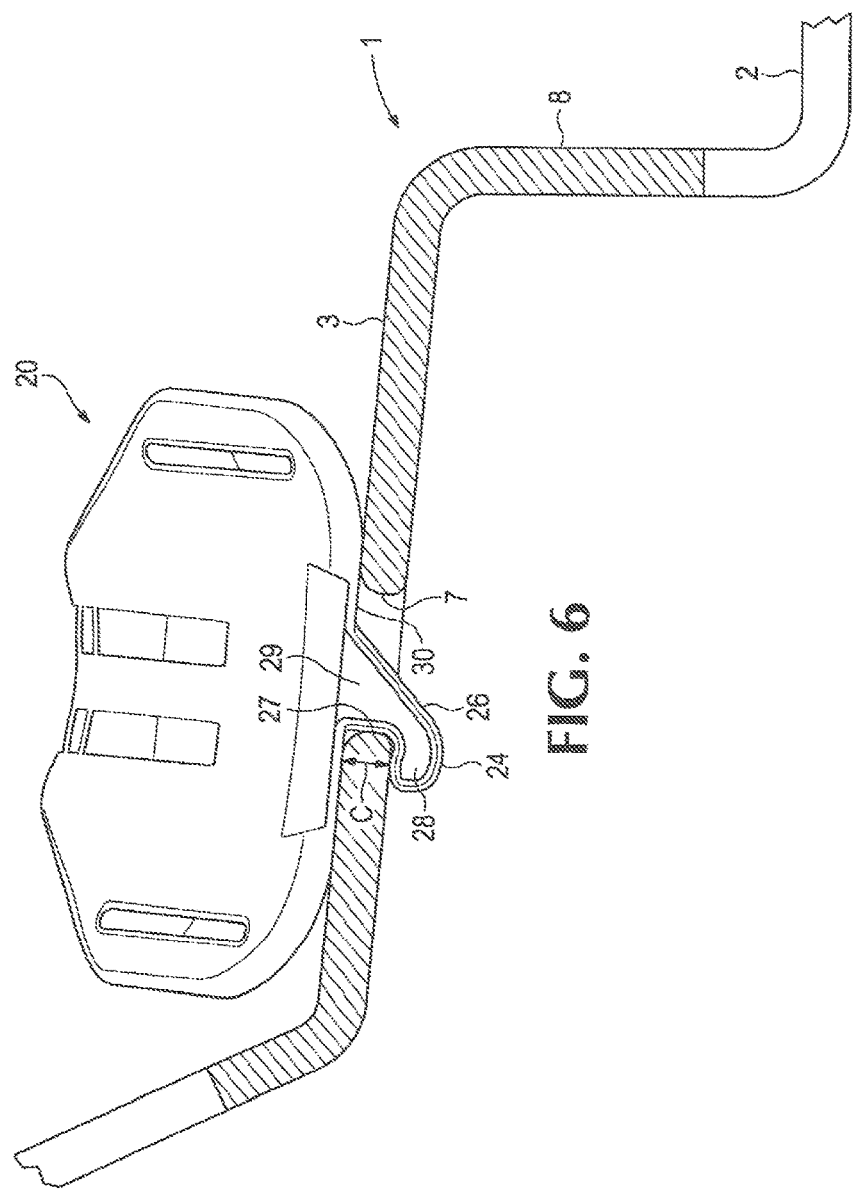

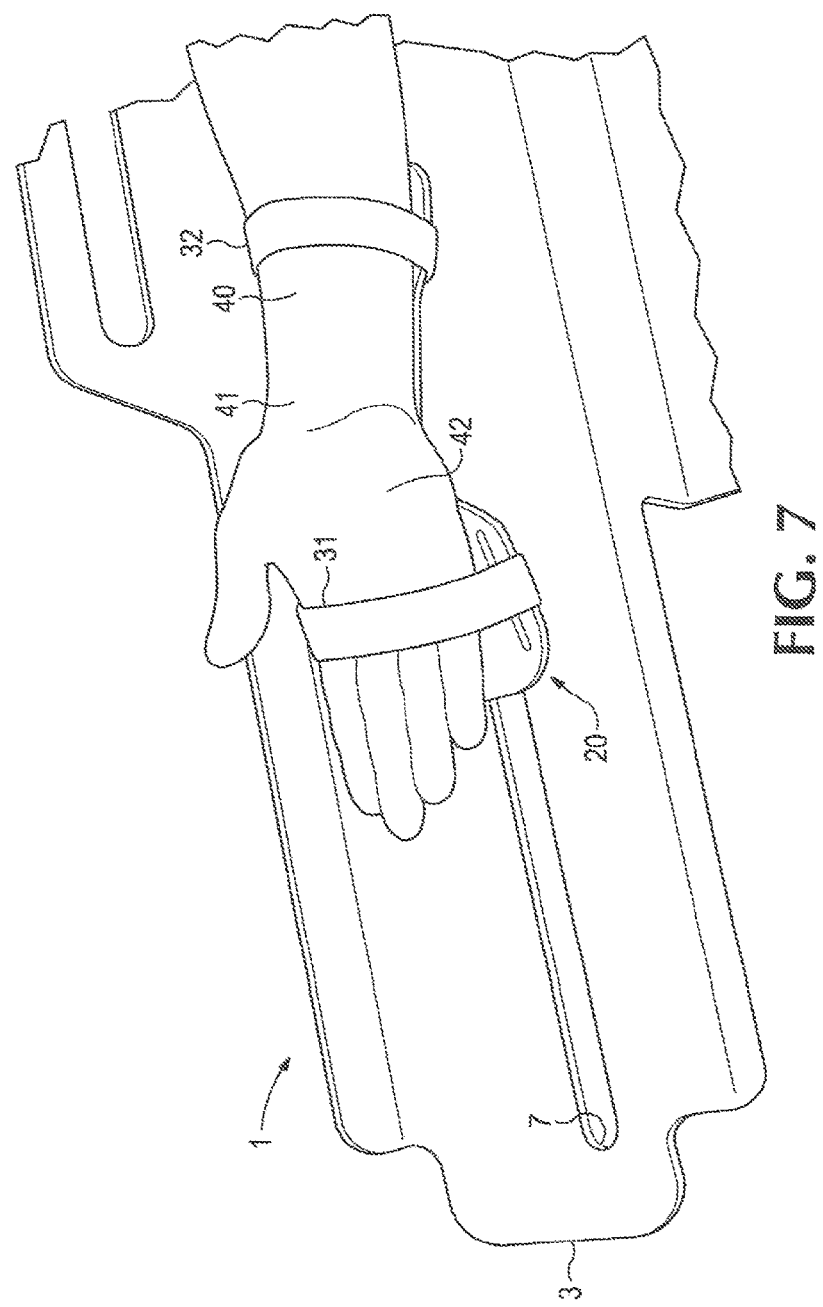

INTEGRATED ARMBOARD AND WRIST SUPPORT APPARATUSES AND METHODS OF USE

RELATED APPLICATIONS

This application is a continuation of pending Non-Provisional application Ser. No. 14/050,729 filed Oct. 10, 2013, which, claims the benefit of U.S. Provisional Application No. 61/795,999 filed Oct. 31, 2012. This Continuation application claims priority of these previously filed applications, the contents of which are incorporated herein by this reference.

The Specification and Drawings herein are the same as presented in Non-Provisional application Ser. No. 14/050,729 except for a correction to a reference to a section view in FIG. 1. The Claims presented herein relate only to a wrist support device, its connector and a means of removable connection to a separate armboard and are different from those presented in Non-Provisional application Ser. No. 14/050,729.

FIELD OF THE INVENTION

The invention relates generally to the field of medicine. More particularly, the invention relates to medical procedures conducted in an interventional radiology or interventional cardiology laboratory, or in a surgical suite. These procedures, during which a patient lies supine on a procedure table, include open surgical procedures, and vascular access procedures used to gain to access to blood vessels for the purpose of percutaneously passing catheters and other devices and substances into the body.

BACKGROUND OF THE INVENTION

Surgical and interventional radiology procedures involving the forearm, wrist or hand require varying degrees of support and immobilization of the extremity. A patient is placed in supine position on a mattress on top of a procedure table and their arm on which the procedure is to be performed is placed on an armboard, which is used to support and position the arm appropriately for the procedure and in some cases immobilize it to varying degree. Procedure tables used for surgical or interventional procedures may have such an armboard attached to them, or may have a separate armboard which is attached to the procedure table semi-permanently or at the time the procedure is performed on the patient.

Wrist supports, which may include makeshift assemblies of materials or devices specifically designed to support the wrist and hand, are also often deployed to position and limit motion of the wrist and hand. An example of a device designed for this purpose is found in pending application U.S. Ser. No. 13/199,821, "Apparatus and method of use for a wrist extension brace" by Benz et al, which has a filing date of Sep. 9, 2011. Additional examples are found in U.S. Pat. No. 4,798,199 by Hubbard and Brunson and in U.S. Pat. No. 5,845,643 by Vergano and Kovacs.

Procedure tables have mattresses that are placed on top of the table. These mattresses typically measure between one and three inches in thickness. The armboards are usually positioned so that their top surface is placed generally at the level of the procedure table, below the level of the top surface of the mattress; often the armboards are slid under the mattress with an arm platform portion protruding at the side of the mattress, with the patient's weight holding the armboard in place. An example of this kind of armboard is found in U.S. Pat. No. 8,369,933 by Crisco and Goff that describes a "substantially planar member" desirably including "both a radiolucent portion and a radiopaque portion". Another armboard is found in pending application U.S. Ser. No. 11/962,767 by Kim, that describes an arm support that can be rotated "about an axis substantially coaxial with the patient's arm", and having a locking mechanism and a bracket for attaching the arm support to a patient support, i.e. a surgical table. Since the top surface of these kinds of armboards is below the top level of the mattress, the patient's arm rests below the level of the shoulder when the patient is supine upon the procedure table, putting stress on the shoulder joint and creating discomfort for the patient. Towels or drapes or pads are often placed on top of the armboard under the arm to raise the level of the patient's arm to relieve discomfort and to properly position the procedure site for the clinician.

The hand is usually taped in a straight, supine-position onto the top surface of the armboard, immobilizing it, often with the wrist in extension. Though necessary for enabling proper clinician access for surgical and vascular access procedures in the hand, wrist and forearm, this arm positioning creates discomfort for the patient: while the forearm, wrist and hand naturally tend to pronate when the patient is in supine position with their arm at their side, during these procedures the entire arm is straight and rotated laterally stressing the wrist, elbow and shoulder joints.

Since many procedures on the forearm, wrist and hand are performed while the patient is conscious, the degree of patient comfort becomes increasingly important with procedures of long duration, i.e. certain surgical or interventional procedures. If discomfort is excessive this can cause difficulty for both the patient and clinician during the procedure. Because the patient's hand is taped to the armboard and covered by a sterile drape during the entire procedure, it is difficult to remove the tape to allow the hand to pronate. Further, allowing the hand to move freely is undesirable since the wrist and hand should be immobilized during and sometimes after the procedure, i.e. to prevent tree movement of the hand at the wrist since this can jeopardize devices inserted into a vascular puncture in the wrist, forearm or hand.

There is a need for an integrated system including armboard and wrist support devices to provide proper clinician access to the surgical or vascular access site on a forearm, wrist or hand, while improving patient comfort. At the time of this application there are no armboard or wrist support devices having the features described for the present invention.

Specific objectives of the invention include: i) providing a surface on which a patient's subject arm rests that is at least at the height of the top surface of the mattress on a procedure table; ii) removable and adjustable deployability onto a procedure table for a range of patient sizes normally encountered in a surgical or interventional setting; iii) enabling hand pronation at any time following commencement of the procedure.

BRIEF SUMMARY OF THE INVENTION

A preferred embodiment of the present invention includes the following: i) an armboard having a base and an arm platform, the base to be placed under the mattress on top of a procedure table, the arm platform to be used to support the arm of a patient lying on top of the mattress, the arm platform being raised above the horizontal plane of the base by a certain height that positions the patient's arm above said horizontal plane, and the arm platform including an integral connection means by which a wrist support device may be removably connected to the armboard; ii) a wrist support device, which may be removably connected to the armboard by an integral connection means, that is attached to the patient and restrains and positions their forearm, wrist or hand for a surgical or vascular access procedure performed on said forearm, wrist or hand. By elevating the position of the patient's arm on the armboard and by enabling expeditious removal of the wrist support device from the armboard using the removable connection means at any time before, during or after the procedure, patient discomfort is alleviated while proper positioning of the forearm, wrist, and hand is enabled when needed for the clinician. The patient's arm remains resting on the arm platform, but is free to move into a more natural position, e.g. pronate position with elbow bent.

BRIEF DESCRIPTION OF THE DRAWINGS

FIG. 2 shows an end perspective view of the armboard 1.
FIG. 3 shows a top perspective view of a wrist support 20.
FIG. 4 shows a front end view of the wrist support 20, with detail shown for a connector 24.
FIG. 5 shows a side view of the wrist support 20.
FIG. 6 shows the section 6-6 view of the wrist support 20 removably connected to the armboard 1 with the connector 24 inserted into the slot 7, which is taken from FIG. 1.
FIG. 7 shows a partial view of the wrist support 20 removably connected to the armboard 1, with hand 42, wrist 41 and forearm 40 removably attached to the wrist support 20.

DETAILED DESCRIPTION OF THE INVENTION

Figure 1:
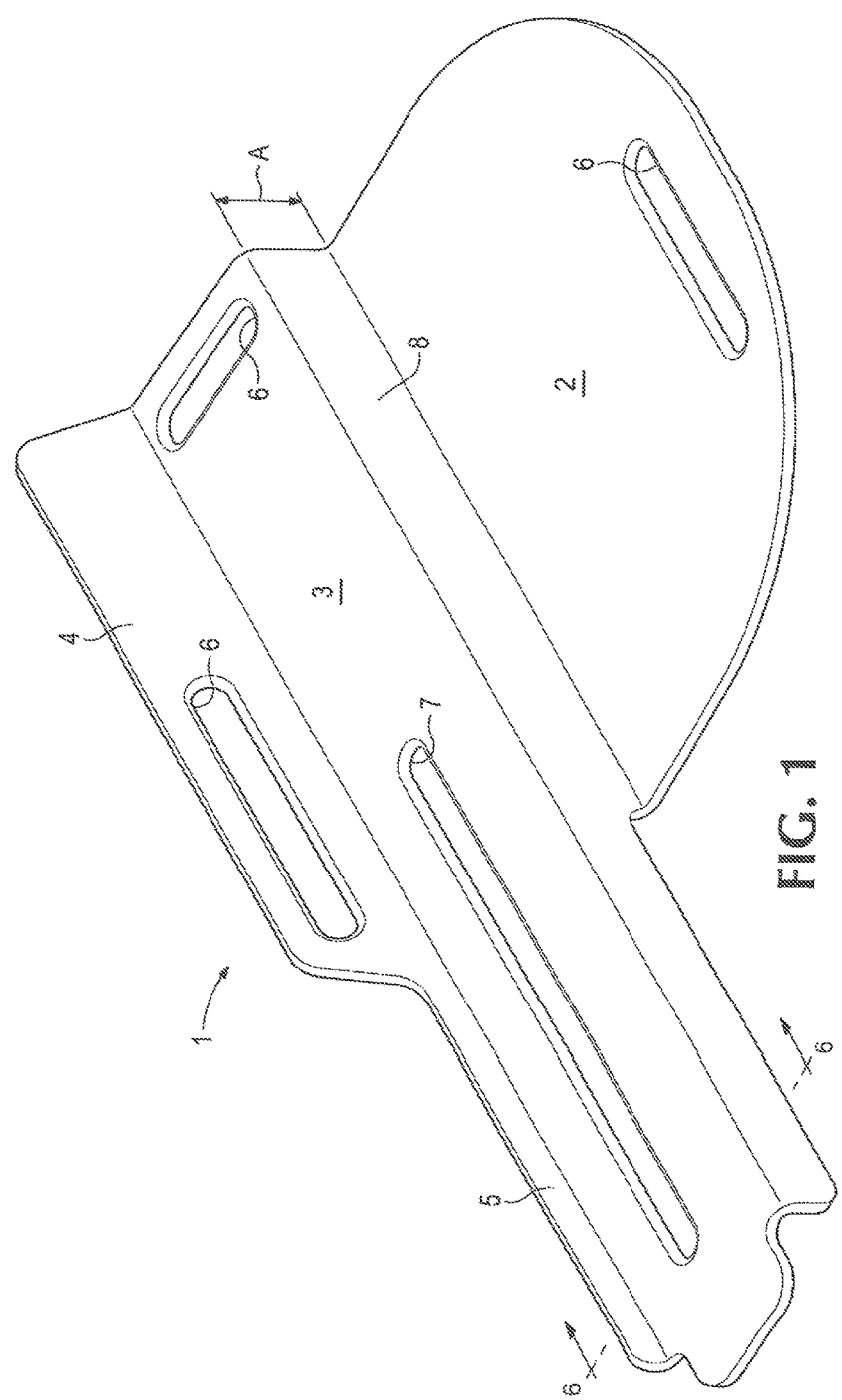
FIG. 1. shows atop perspective view of an armboard 1.

FIG. 1 shows a top perspective view of an armboard 1 that includes at minimum a base 2, an arm platform 3, and connector slot 1, the flat expanse of base 2 being generally in the horizontal plane. Other elements which may be further included are an upper arm rail 4, a forearm rail 5, and at least one handhold 6, although these are not essential to the core function of the armboard 1. The rails 4 and 5 serve as a barrier to help retain the patient's arm on the arm platform 3. The handholds 6 enable an operator to easily carry and position the armboard 1. The base 2 is placed under a mattress of a procedure table so that the armboard 1 is held in place by the weight of a patient who lies on top of the mattress. The base 2, being flat as shown in the Figures, and having no features for securement to the table other than the force of the weight of the mattress and patient resting upon it, thereby permits removable and adjustable deployment onto the procedure table under the mattress. In this embodiment the arm platform 3 extends out from under the right side edge of the mattress and supports the patient's right arm, which generally is in a supine or pronate position. Notably the plane of the arm platform 3, i.e. of the flat portion on which the patient's arm rests, is elevated above the level of the plane of base 2 by height A of a vertical member or wall 8 such that the patient's arm rests in a position above the horizontal plane of the top of the procedure table during deployment. Height A may be selected from the range of 0.5 inches to 5.0 inches. Although the vertical member 8 is shown continuously connected along the entire length of the base 2, it is within the scope of the invention that there may be multiple vertical members 8 discontinuously connected along the length of base 2 to arm platform 3. In alternative embodiments the arm platform 3 is not necessarily positioned completely horizontally, nor is it necessarily flat along its entire upper surface; further, the elevation of the arm platform 3 above the base 2 may be adjustable by a user, i.e. height A may be variable. In addition the arm platform 3 may be angled side to side or from one end to the other; such angle may be at one side or the other or one end or the other, or may be at a midpoint on the surface of the arm platform 3. The upper arm rail 4 and forearm rail 5 help keep the patient's arm from moving laterally off the arm platform 3. The rails 4 and 5 may be at angles not perpendicular to the arm platform 3, as shown in FIG. 1, however the angle of the rails 4 and 5 may also be perpendicular to the arm platform 3. The handholds 6 may be of varying size and shape and are for the purpose of carrying and positioning the armboard 1 or for securing straps or other accessories. The connector slot 7, an opening having a length and width and passing entirely through the arm platform 3 from its top surface to its bottom surface, engages with a connector 24 on a wrist support device 20, so as to enable rapid removable connection with said wrist support device 20. A view 6-6 is indicated at the distal end of the arm platform 3, this section view shown in FIG. 6. Because of its non-symmetrical shape, the embodiment shown in this FIG. 1 is for a right-side-only armboard, though a left-side-only version is within the scope of this invention by simply making a mirrored version of the embodiment shown.

FIG. 2 shows an end perspective view of the armboard 1 having a base 2, and a vertical wall 8 supporting an arm platform 3 that is positioned at a height A above the base 2. In this embodiment, the plane of arm platform 3 is oriented at an angle B to the plane of the base 2 or the horizontal plane, said angle B being selected from the range of 0.1° to 50.0°. Thus the plane of the arm platform 3 is oriented at an angle from the horizontal plane that is different from that of the base 2, more particularly in this embodiment the height above base 2 of the lateral side of the arm platform 3 is greater than the height of the medial side of the arm platform 3 due to angle B.

FIG. 3 shows a top perspective view of a wrist support device 20 having at minimum a hand section 21, a forearm section 22, and a connector 24. Other elements which may be included are an apex 23 and structural ribs 25, although these are not essential to the core function of the wrist support 20. The ribs 25 provide structural stiffness enabling less material to be used in the forming of the wrist support 20. The apex 23 forms an angle that enables extension of the patient's wrist 41 to enable proper access by the clinician for some kinds of medical procedures, including cannulation of the radial artery, during deployment of the wrist support 20. In alternative embodiments, the wrist support 20 may be flat, i.e. the apex 23 will be absent. The connector 24 enables rapid removable connection with the armboard 1 and further includes an angled side 26. The wrist support 20 may further include an optional removable pad for patient comfort, that can be replaced, and wrist straps for securement to a patient's arm. All or part of the wrist support can be for one-time use or alternatively may be cleaned and re-used.

FIG. 4 shows a front end view of the wrist support 20 with further detail shown of the connector 24, which in this embodiment is in the form of a hook that includes an angled side 26, an interior hook 27, a hook tip 28 and main body 29.

The base of the hook extends from the flat front edge 30 downward, this front edge 30 being located on the bottom surface at the distal end of the hand section 21. The angle of angled side 26 is selected from the range of 1° to 89° relative to the horizontal plane of the front edge 30. The top of the hook tip 28 is positioned at a distance C from the bottom of the front edge 30. The angled side 26 and rounded surface of hook tip 28 enable easy removable attachment of the wrist support 20 into the slot 7 of the armboard 1 by making it easy to slide the wrist support 20, when attached to a patient's hand and placed medially to, i.e. to the left of, the slot 7, across the top surface of the arm platform 3 laterally, i.e. to the right, until it drops into the slot 7, the angled side 26 guiding the movement of the connector 24 such that the top of the hook tip 28 engages with the bottom surface of the arm platform 3 immediately lateral to, i.e. to the right of, the slot 7, and the interior hook 27 engages with the interior edge of slot 7. This keeps the wrist support 20 in place, preventing movement in the longitudinal axis and in the vertical direction. The thickness of the arm platform 3 surrounding the slot 7 is generally the same as or very slightly smaller than the distance C. Further, the angled side 26 makes it easy to detach the wrist support 20 from the slot 7 by guiding the connector 24 out of the slot when the wrist support is pushed in the medial direction, i.e. to the left, by a user. When thusly pushed, the lateral pushing force is converted to upward motion by the angled side 26, thereby moving the connector 24 both laterally and upwards so that the top surface of the hook tip 28 and interior hook 27 disengage from the bottom surface of the arm platform 3 and interior edge of slot 7, respectively. The orientation of the hook and the direction of pushing may also be reversed in an alternative embodiment.

FIG. 5 shows a side view of wrist support 20 and shows further detail of the ribs 25, and the location of the apex 23, which is where the wrist is positioned. The top and bottom surfaces of hook tip 28 on connector 24 are shown to be rounded in shape, distance C being taken from the apex of the rounded top surface of hook tip 28. These rounded surfaces, though optional, enable easier movement of the connector 24 into and out of the slot 7.

FIG. 6 shows the front end section 6-6 view, taken from FIG. 1, of the wrist support 20 removably connected to the armboard 1. The wrist support 20 is shown removably connected to the arm platform 3 that is permanently connected by the fixed-height vertical member 8 to the base 2 of the armboard 1. The removable connection is achieved by the insertion of the connector 24 into the slot 7. The top surface of the hook tip 28 and interior hook 27 are shown generally engaging with the bottom surface of the arm platform 3 and interior edge of the slot 7, respectively. The angled side 26 does not touch any of the edges of slot 7 when the interior hook 27 and top surface of the hook tip 28 fully engage with the lateral edge of slot 7 and the bottom surface of arm platform 3, respectively, as shown. The front edge 30 rests on the top surface of the arm platform 3, thus the connector 24 captures the top and bottom surfaces of the arm platform 3 adjacent the edge of the slot 7, the front edge 30 on the top surface, the top surface of the hook tip 28 on the bottom surface, the thickness of the arm platform between these surfaces generally similar to the distance C.

FIG. 7 shows a partial view of a hand 42, wrist 41 and forearm 40 positioned on wrist support 20, which is removably connected to the slot 7 of the arm platform 3 of the armboard 1, such removable connection as shown in FIG. 6. A hand strap 31 and forearm strap 32, each having two ends, secure the hand 42, wrist 41 and forearm 40 to the wrist support 20. The straps 31 and 32 are, at one end, removably attached to the wrist support 20, using any of several removably attachable connection means, in this embodiment by the use of a VELCRO hook and loop materials. Similar removably attachable connection means are used to secure the straps 31 and 32, at their opposite ends, around the hand 42 and forearm 40. To removably attach the wrist support 20 to the patient, it is applied to the dorsal surface of the forearm 40, wrist 41 and hand 42. The straps 31 and 32 are wrapped around the palmar or volar surfaces of the forearm 40, wrist 41 and hand 42 so that the straps' 31 and 32 free ends are placed on the underside of the wrist support 20, where they are attached by pressing the loop material of said straps 31 and 32 onto mating hook material placed on the underside of the wrist support 20. To detach the wrist support 20 from the patient the ends of the straps 31 and 32 are pulled away from the hook material on the underside and if is then removed. The connector 24 and slot 7 thus comprise elements of an integral connection means for the removable connection of the wrist support 20 to the armboard 1.

Figure 8:
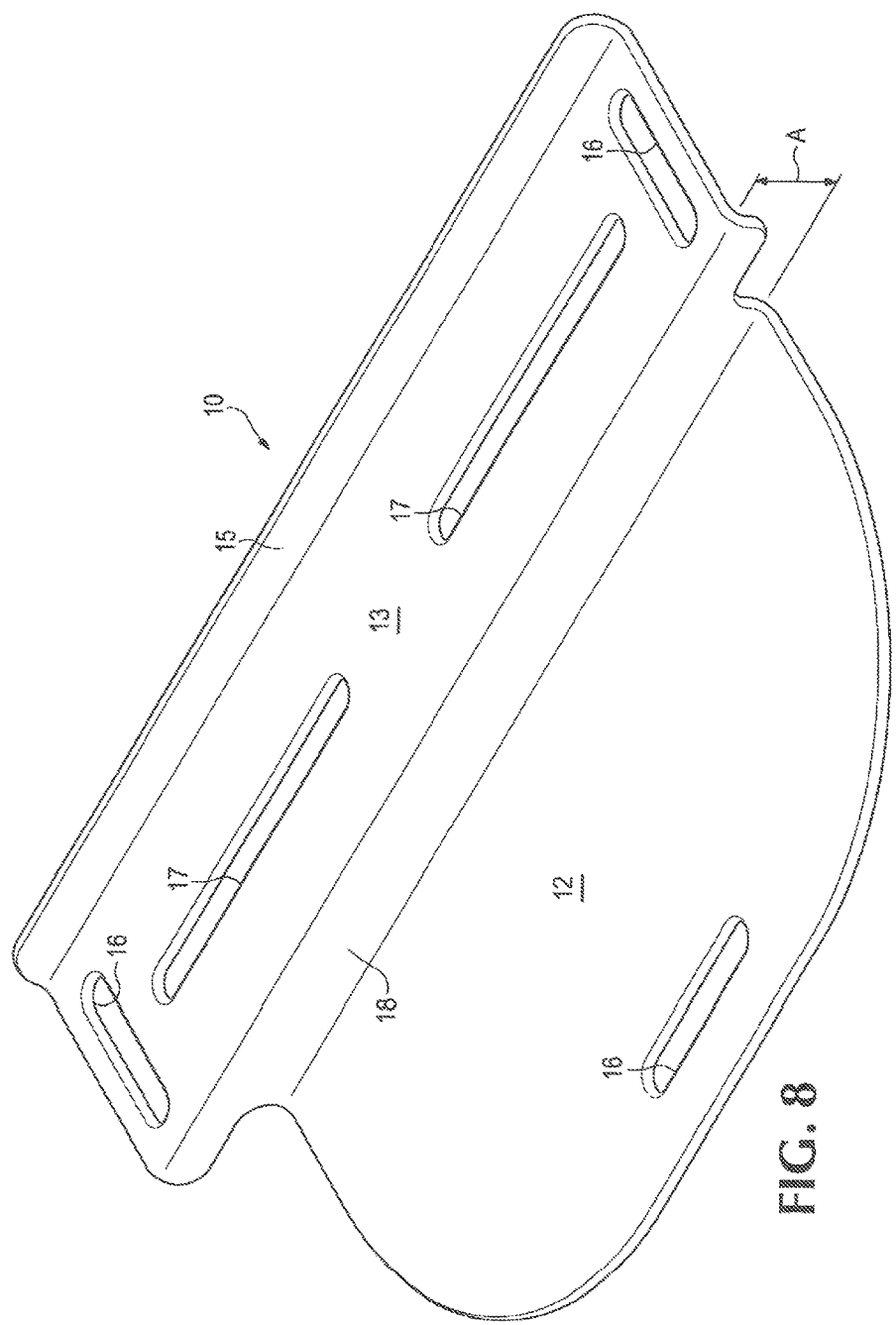
FIG. 8 shows a top perspective view of an alternate embodiment of an armboard 10.

FIG. 8 shows a top perspective view of an alternate embodiment of the invention, i.e. an armboard 10, which includes a base 12, and an arm platform 13 attached to the base 12 by a vertical member or wall 18, the vertical member or wall 18 having a height A and the arm platform having at least one slot 17, the armboard 10 having a symmetrical shape. A rail 15 and handholds 16 may also be optionally included. The shape of armboard 10 can be described as having a symmetrical shape in this embodiment since, if a single line is drawn through the center of the armboard 10 that bisects each of the base 12, arm platform 13 and handhold 16 of the base 12 into two halves, at any point along their widths the lengths of these halves would be the same.

Thus two embodiments, i.e. armboard 1 and armboard 10, of the same invention are presented. The armboard 1 is intended for deployment under the mattress of a procedure table on which a patient lies such that the arm platform 3 is located on the right side of the mattress to support the patient's right arm. Deployment of a right-side-only version, which is shown in the Figures, permits placing the base 2 under the mattress only on the right side the table. A left-side-only version, a mirror of the right-side-only version, permits placing the armboard 1 only on the left side of the table. The armboard 10, a dual-side version, is also intended for deployment under the mattress of a procedure table on which a patient lies, but the symmetrical shape of the base 12 and arm platform 13 enables the armboard 10 to be deployed on either side of the procedure table to support either the patient's right arm or left arm; deployment for the left arm support involves placing the base 12 under the mattress on the left side the table. Other features of the armboards 1 and 10 are intended to be the same, particularly including the presence of a height A, an angle B and the removable connectability with the wrist support 20 enabled by the slots 7 and 17 and the connector 24, this removable connectability having identical operation for both embodiments, i.e. for both armboard 1 and armboard 10.

To removably connect the wrist support 20 to the armboard 1 (or armboard 10), the wrist support 20 is first attached to the patient and after clinical preparation the patient's arm, palm facing up, is placed generally onto the distal portion of the arm platform 3. Thusly placed, the connector 24, or hook-shaped connector element, may be inserted into slot 7, or slot element, to removably connect wrist support 20 to arm platform 1. To make such insertion, the hand 42 and attached wrist support 20 are moved so that the connector 24 is positioned medial, i.e. to the left (from the patient's perspective) of the slot 7. The operator then presses gently down while moving the hand 42 in the lateral direction, i.e. to the right until the bottom surface of the hook tip 28 drops into the slot 7. Said bottom surface may be rounded to make such slidable movement easy. The angled side 26 then engages with the medial, i.e. left, edge of the slot 7 and rides downward on said edge, the force exerted by the operator guiding the connector 24 laterally and downwards until: i) the front edge 30 of the wrist support 20 engages with the top surface of the arm platform 3, ii) the top surface of the hook tip 28 engages with the bottom surface of the arm platform 3 adjacent the lateral i.e. right edge of slot 7, and iii) the interior hook 27 engages with the lateral edge of slot 7. Thus the connector 24 captures the top and bottom surfaces of the arm platform 3 and the lateral edge of slot 7; since distance C is similar to the thickness of the portions of arm platform 3 adjacent the lateral edge of slot 7, a secure removable connection of wrist support 20 to armboard 1 is achieved. Where said thickness is the same as or greater than the distance C, such fit shall be snugly achieved, in particular where the material of the connector 24 permits slight vertical deflection of the hook tip 28 during engagement with arm platform 3. Therefore this embodiment includes two elements of an integral connection means, a generally hook shaped connector element, or connector 24, and a slot element, or slot 7.

To detach the wrist support 20 from the armboard 1, the operator pushes the hand 42 in the medial direction, i.e. to the left or towards the patient's body. The wrist support 20 and connector 24 move in the medial direction only in the horizontal plane until the angled side 26 engages with the medial edge of slot 7 at which time the pushing force in the medial direction causes the connector 24, and therefore the entire wrist support 20 and attached hand 42, to also move in the vertical plane, i.e. upwards, as the angled side 26 rides over the medial edge of slot 7. Said pushing force simultaneously causes the top surface of the hook lip 28 and interior hook 27 to disengage from the bottom surface of arm platform 3 and lateral edge of slot 7, respectively. The operator continues to push on the hand 42 in the medial direction until the bottom surface of the hook tip 28 rides over the medial edge of slot 7 and onto the top surface of arm platform 3 medial to the slot 7, sliding easily because of the rounded feature of the bottom surface of the hook tip 28. The wrist support 20 is thusly detached from the armboard 1. Such removable connection of the wrist support 20 to the armboard 1 or armboard 10 enables the operator to release the patient's hand 42 from a supine position, thereby allowing it to pronate while still immobilizing the wrist 41 and hand 42; because the operator need only push to detach the wrist support 20 from the armboard 1 or 10, such detachment may be performed at any time following commencement of the procedure even when the wrist 41 and hand 42 are covered by a sterile drape.

Although these embodiments, i.e. armboard 1 and armboard 10, demonstrate an integral connection means comprising a generally hook-shaped connector 24 on the wrist support device 20 removably engaging in a slot 7 or 17 on the armboards 1 or 10, many other types of similarly removable integral connection means, comprising at least one element of such connection means located on each of the armboards 1 and 10, and wrist support 20, can be envisioned by those skilled in the art. These include any of the following taken singly or in combination and apply to configurations including the wrist support 20 and both the armboard 1 and armboard 10: a ball and socket connection, with the ball on the wrist support 20 and socket on the armboard 1 or vice versa, alternatively with one or both of these elements placed in multiple locations on the arm platform 3 or 13 of the armboard 1 or 10; a peg and notch connection, with one element on the wrist support 20 and the other on the armboard 1; a hook or knob or other protrusion on the wrist support 20 and a rail with detents or notches or holes in which the hook or knob or other protrusion would fit on the armboard 1; a hook or knob or other protrusion on the wrist support 20 and one or more holes or indents in which the hook or knob or other protrusion would fit on the armboard 1 or 10; a clasp, hook or knob or key or other protrusion on the wrist support 20 that mates with a groove or slot or keyhole on the armboard 1; a releasable clamp on the wrist support 20 that engages with an edge or slot or rail or tab located on the armboard 1; a releasable clamp on the armboard 1 that engages with an edge or slot or rail or tab located on the wrist support 20; a suction cup located on the wrist support 20 that can be removably adhered to a surface of the armboard 1; a strap attached to wrist support 20 that secures into one or more holes or slots or notches on armboard 1 or that wraps around the arm platform 3 or 13.

The armboard 1 or 10 and wrist support 20 may be composed of any rigid material including more particularly a non-magnetic material generally transparent to ionizing radiation, including x-rays, i.e. having a radiolucent property. Such transparency enables x-ray visualization of the vessels in the forearm 40 and wrist 41 during a radial access procedure, more particularly the radial artery and vessels adjacent the radial artery, in the event that such visualization is required to successfully access other vessels via the radial artery, a not-uncommon requirement particularly for those clinicians new to radial access. The material of the armboards 1 or 10 may also be transparent in the visible light spectrum and fabricated of multiple layers or in a single layer, for example cut and formed from a sheet of transparent, rigid, radiolucent plastic such as acrylic, polycarbonate or polyethylene.

Dimensions generally described herein apply to both the armboard 1 and armboard 10. Unless the meaning is clearly to the contrary, all ranges set forth herein are deemed to be inclusive of the endpoints. Certain dimensions of the arm platforms 3 and 13 are generally selected from the range of fifteen to sixty inches long, and from the range of three to twelve inches wide. Certain dimensions of the bases 2 and 12, in a generally rectangular shape, are generally selected from the range of three inches to thirty inches on each side, or in a generally circular shape from the range of four to forty inches in its diameter. The height A is a certain dimension generally selected from the range of 0.25 inches to six inches. Certain dimensions of the wrist support 20 are generally selected from the ranges of three to twenty inches long and two to eight inches wide. The thickness of the armboards 1 and 10 is generally similar to the distance C and may generally be in the range of 0.005 inches to two inches, the armboards 1 and 10 having no requirement that said thickness be uniform across all of its surface. Distance C may therefore also generally be selected from the range of 0.005 inches to two inches. The slots 7 and 17 have a width as measured from the inner most edges that is selected from the range of 0.1 inch to two inches, and a length that is selected from the range of 3 inches to 30 inches, the length for the purpose of accommodating patients of varying size and the width for the purpose of engaging with a connector 24. Armboards 1 and 10 both show a device that has all of these dimensions fixed, i.e. non-changeable by a user; it is within the scope of this invention that for other embodiments some of these dimensions may be adjusted by the user, for example, by having instead of a unitary construction, a multi-part adjustable construction that permits the height A or the length of the arm platforms 3 or 13 to be changed by the user.

Angle B, an optional feature, raises the lateral edge of the arm platform 3 relative to its medial edge (i.e. the edge adjoining the vertical member 8) by an angle selected from the range of 0.1° to 50.0°. This has the effect, when the wrist support 20 is attached to the hand 42 and to the arm platform 3, of placing the hand 42 in a partially pronated position without having the wrist support 20 detached from the armboard 1. Although not specifically shown in the Figures, Angle B may also be present in armboard 10. Angle B is shown and described as fixed, i.e. non-changeable by an operator, however, by having instead of a unitary construction, a multi-part adjustable construction that includes a hinge between the arm platform 3 and the vertical wall 8, and a manual fixation means to fix the arm platform 3 in place following such adjustment, the angle B may be changed by an operator and such attribute is within the scope of this invention.

A method of use of the present invention comprises the following general steps that include actions, in serial order, previously described in the background and specification sections herein; such steps apply to both the armboard 1 and armboard 10: i) the wrist support 20 is removably attached to the patient's forearm 40, wrist 41 and hand 42; ii) the wrist support 20 is then removably attached to the armboard 1 by placing the connector 24 into the slot 7; iii) the site on the forearm 40, wrist 41 or hand 42 are prepared in accordance with the type of medical procedure to be performed. The method of use may optionally further include: iv) removal of the wrist support 20 from the armboard 1 during or after completion of the medical procedure; v) post-procedure cleansing of the site on the forearm 40, wrist 41 or hand 42; vi) transport of the patient to a recovery area with the wrist support continuing to be attached to the forearm 40, wrist 41 or hand 42 and remaining in place for an extended period of minutes or hours after the completion of said procedure, to facilitate any healing process of the site, for example, hemostasis of a vascular puncture site.

It will be understood that the present invention is not limited to the method or detail of construction, fabrication, material, application or use described and illustrated herein. Indeed, any suitable variation of fabrication, use, or application is contemplated as art alternative embodiment, and thus is within the spirit and scope, of the invention.

It is further intended that any other embodiments of the present invention that result from any changes in application or method of use or operation, configuration, shape, size, user-configurability, or material, which are not specified within the detailed written description or illustrations contained herein yet would be understood by one skilled in the art, are within the scope of the present invention.

Finally, those of skill in the art will appreciate that the invented apparatus, system and method described and illustrated herein may be developed, manufactured and implemented in any of several different ways.

Accordingly, while the present invention has been shown and described with reference to the foregoing embodiments of the invented apparatus, it will be apparent to those skilled in the art that other changes in form and detail may be made therein without departing from the spirit and scope of the invention as defined in the appended claims.

We claim:

1. A wrist support device for use in surgical or interventional or vascular cannulation procedures that is removably attachable to an armboard, a portion of which is placed under a procedure table mattress, the wrist support device comprising at least a hand section, a forearm section, and a single hook-shaped connector, wherein:
   the connector further includes at least a base, a main body, an angled side, an interior hook, and a hook tip;
   the hand section has a distal end that includes at least a flat front edge located on its bottom surface;
   the connector is attached at its base only to the flat front edge of the bottom surface of the distal end of the hand section;
   no part of the connector moves independently of or relative to the wrist support device;
   the main body extends downward from the base;
   the hook tip has a top side and a bottom side;
   an opening is located on the main body opposite the angled side, said opening extending a distance from the top side of the hook tip to the bottom surface of the distal end of the hand section;
   the connector is removably attachable into a slot, which is disposed between a top surface and a bottom surface of an arm platform of the armboard, by a slidable movement of the bottom side of the hook tip laterally across the top surface of the arm platform towards the slot and then a downward and lateral movement enabled by the angled side slidably moving against an interior side of said slot;
   the top side of the hook tip is capable of engaging with the bottom surface of the arm platform that is adjacent the slot and the interior hook is capable of engaging with an interior edge of the slot opposite the interior side against which the angled side is configured to move to secure the connector inside the slot;
   the bottom surface of the distal end of the hand section rests on a portion of the top surface of the arm platform that surrounds the slot and the angled side is angled away from the interior side of the slot while the connector is attached into the slot.

2. The wrist support device of claim 1, wherein the top side and bottom side of the hook tip are rounded to facilitate slidable movement against a surface of the arm platform.

3. The wrist support device of claim 1, wherein the connector may be detached from the slot by slidably moving said device laterally such that the angled side slidably moves against the interior side of the slot, thus guiding it upwards and laterally.

4. The composition of the wrist support device of claim 1 more particularly comprising a material transparent to ionizing radiation.

5. The wrist support device of claim 1 that further includes an apex for the purpose of extending a patient's wrist during deployment of said device.

6. The wrist support device of claim 1 wherein the distance from the top side of the hook tip to the bottom side of the flat front edge of the distal end of the hand section is between 0.005 inches and 2 inches.

7. The wrist support device of claim 1 that further includes at least one strap for the purpose of removable attachment to a wrist.

8. A hook-shaped connector located on a wrist support device for use in surgical or interventional or vascular cannulation procedures that enables removable attachment to an armboard, a portion of which is placed under a procedure table mattress, the wrist support device including at least a hand section having a distal end, the armboard including at least an arm platform, and the connector including at least a base, an angled side, an interior hook, a hook tip, and a main body, wherein:

a flat front edge is located on a bottom surface of the distal end of the hand section;

the connector is attached at its base only to the flat front edge on the bottom surface of the distal end of the hand section;

the main body extends downward from the base;

the hook tip includes a top side and a bottom side;

an opening is located opposite the angled side, said opening extending a distance from the top side of the hook tip to the bottom surface of the distal end of the hand section;

the connector is removably attachable into a slot, which is disposed between a top surface and a bottom surface of the arm platform, by a slidable movement of the bottom side of the hook tip laterally across the top surface of the arm platform towards the slot and then a downward and lateral movement enabled by the angled side slidably moving against an interior side of said slot;

the top side of the hook tip is capable of engaging with the bottom surface of the arm platform that is adjacent the slot and the interior hook is capable of engaging with an interior edge of the slot opposite the interior side against which the angled side is configured to move to secure the connector inside the slot;

the bottom surface of the distal end of the hand section rests on a portion of the top surface of the arm platform that surrounds the slot and the angled side is angled away from the interior side of the slot while the connector is attached into the slot.

9. The connector of claim 8, wherein the top side and bottom side of the hook tip are rounded to facilitate slidable movement against a surface of the arm platform.

10. The connector of claim 8, which more particularly may be detached from the slot by slidably moving said device laterally such that the angled side slidably moves against the interior side of the slot, thus guiding it upwards and laterally.

11. The connector of claim 8, wherein the distance from the top side of the hook tip to the bottom side of the flat front edge of the distal end of the hand section is between 0.005 inches and 2 inches.

12. An integral connection means for the purpose of removably connecting a wrist support device (20) for use in surgical or interventional or vascular cannulation procedures to an armboard (10), the wrist support device (20) including at least a hand section (21) and the armboard (10) including at least an arm platform (13), wherein:

the integral connection means comprises at least a single hook-shaped connector (24), located on the wrist support device (20), and a slot (17) located on the arm platform (13);

the connector (24) includes at least a base, an angled side (26), an interior hook (27), a hook tip (28), and a main body (29);

the slot (17) is disposed between a top surface and a bottom surface of the arm platform (13);

the connector (24) is attached at its base only to a flat front edge (30) on a bottom surface of a distal end of the hand section (21);

the main body (29) extends downward from the base;

the hook tip (28) includes a top side and a bottom side;

an opening is located opposite the angled side (26), said opening extending a distance (C) from the top side of the hook tip (28) to the bottom surface of the distal end of the hand section (21);

the connector (24) is removably attachable into the slot (17) by a slidable movement of the bottom side of the hook tip (28) in a lateral direction across the top surface of the arm platform (13) towards the slot (17) and then a downward and lateral movement enabled by the angled side (26) slidably moving against a medial interior side of said slot (17);

the top side of the hook tip (28) is capable of engaging with the bottom surface of the arm platform (13) that surrounds the slot (17) to secure the connector (24) inside the slot (17);

the bottom surface of the distal end of the hand section (21) rests on a portion of the top surface of the arm platform (13) that surrounds the slot (17) while the connector (24) is attached into the slot (17).

13. The integral connection means of claim 12, wherein the top side and bottom side of the hook tip (28) are rounded to facilitate slidable movement against a surface of the arm platform (13).

14. The integral connection means of claim 12, wherein the connector (24) may be detached from the slot (17) by slidably moving said device (20) in a medial direction such that the angled side (26) is configured to slidably move against the medial interior side of the slot (17), thus guiding it upwards and in the medial direction.

15. The integral connection means of claim 12, wherein the distance (C) from the top side of the hook tip (28) to the bottom side of the flat front edge (30) of the distal end of the hand section (21) is between 0.005 inches and 2 inches.

* * * * *